US008461299B2

(12) United States Patent
Ochi et al.

(10) Patent No.: US 8,461,299 B2

(45) Date of Patent: Jun. 11, 2013

(54) PEPTIDE CAPABLE OF BINDING TO IMMUNOGLOBULIN

(75) Inventors: Takahiro Ochi, Kobe (JP); Toshikazu Shiba, Okaya (JP); Osamu Masaki, Osaka (JP)

(73) Assignees: MMT Co., Ltd., Osaka (JP); Takahiro Ochi, Hyogo (JP)

( * ) Notice: Subject to any disclaimer, the term of this patent is extended or adjusted under 35 U.S.C. 154(b) by 429 days.

(21) Appl. No.: 12/733,288

(22) PCT Filed: Aug. 20, 2008

(86) PCT No.: PCT/JP2008/064837

§ 371 (c)(1), (2), (4) Date: Feb. 22, 2010

(87) PCT Pub. No.: WO2009/025300

PCT Pub. Date: Feb. 26, 2009

(65) Prior Publication Data

US 2010/0167348 A1 Jul. 1, 2010

(30) Foreign Application Priority Data

Aug. 21, 2007 (JP) ................................. 2007-214961

(51) Int. Cl.

| | |
|---|---|
| ***C07K 7/06*** | (2006.01) |
| ***A61K 38/08*** | (2006.01) |
| ***C12N 15/12*** | (2006.01) |
| ***G01N 33/53*** | (2006.01) |
| ***G01N 33/543*** | (2006.01) |

(52) U.S. Cl.

USPC ........ 530/329; 536/23.1; 435/320.1; 435/7.1; 422/430; 436/518

(58) Field of Classification Search

None

See application file for complete search history.

(56) References Cited

U.S. PATENT DOCUMENTS

| | | | | |
|---|---|---|---|---|
| 5,260,308 | A * | 11/1993 | Poduslo et al. | 424/141.1 |
| 6,673,561 | B1 * | 1/2004 | Morris | 435/7.92 |
| 2005/0266464 | A1 * | 12/2005 | Marshall et al. | 435/6 |
| 2006/0052292 | A1 * | 3/2006 | Rasmussen et al. | 514/12 |
| 2006/0270598 | A1 * | 11/2006 | Zalevsky et al. | 514/12 |

FOREIGN PATENT DOCUMENTS

| | | |
|---|---|---|
| WO | 03/022992 | 3/2003 |
| WO | 2007/008937 | 1/2007 |
| WO | 2008/035527 | 3/2008 |

OTHER PUBLICATIONS

Machine translation of WO 2008/035527 A1 (Ochi et al.) and accompanying sequence listing, retrieved from http://dossier1.ipdl.inpit.go.jp/AIPN/ on Jul. 10, 2012 (30 pages total).*

Harlow, E. and Lane, D., Antibodies: A Laboratory Manual (1988) Cold Spring Harbor Laboratory Press, Cold Spring Harbor, NY, pp. 23-26.*

Lederman et al. "A single amino acid substitution in a common African allele of the CD4 molecule ablates binding of the monoclonal antibody, OKT4" Mol Immunol. Nov. 1991;28(11):1171-81.*

Colman et al. Research in Immunology, 1994; 145(1): 33-36.*

Office Action issued in corresponding European Patent Application No. 08827673.8 dated Jun. 7, 2011.

English translation of the full text of the Chinese Office Action issued in corresponding Chinese Patent Application No. 200880112469.7, of which was previously cited in an IDS filed on Jun. 11, 2012.

International Preliminary Report on Patentability and Written Opinion (in English) mailed Aug. 18, 2011, in International (PCT) Application No. PCT/JP2010/050539.

English translation of the International Preliminary Report on Patentability and Written Opinion issued Mar. 9, 2010 in International (PCT) Application No. PCT/JP2008/064837.

P. K. E. Trinder et al., "Functional Definition of a B Cell Epitope, KGEQGEPGA, on Clq the Fc-Binding Subunit of the First Component of Complement", Scand. J. Immunol., vol. 50, No. 6, pp. 635-641, 1999.

T. Ochi et al., "Natural Course of Joint Destruction and Fluctuation of Serum Clq Levels in Patients with Rheumatoid Arthritis", Arthritis Rheum.,vol. 31, No. 1, pp. 37-43, Jan. 1988.

C. Gaboriaud et al., "The Crystal Structure of the Globular Head of Complement Protein Clq Provides a Basis for Its Versatile Recognition Properties", The Journal of Biological Chemistry, vol. 278, No. 47, pp. 46974-46982, Nov. 21, 2003.

Supplementary European Search Report dated Sep. 6, 2010 in Application No. EP 08827673.8.

G. C. Sellar et al., "Characterization and Organization of the Genes Encoding the A-, B- and C-Chains of Human Complement Subcomponent Clq", Biochem. J., vol. 274, pp. 481-490, 1991.

J. H. Slingsby et al., "Homozygous Hereditary Clq Deficiency and Systemic Lupus Erythematosus", Arthritis & Rheumatism, vol. 39, No. 4, pp. 663-670, Apr. 1996.

Chinese Office Action dated Apr. 12, 2012 issued in corresponding Chinese Patent Application No. 200880112469.7 and an English translation thereof.

Office Action dated Jan. 27, 2009 issued in Japanese Patent Application No: 2008-547804 with English translation.

Office Action issued Aug. 23, 2012 in corresponding European Patent Application No. 08 827 673.8, (four pages).

Office Action issued in Chinese Patent Application No. 201080014036.5 issued Jul. 30, 2012 with English abstract.

* cited by examiner

*Primary Examiner* — Christine Foster

(74) *Attorney, Agent, or Firm* — Wenderoth, Lind & Ponack, L.L.P.

(57) ABSTRACT

Disclosed are: a peptide capable of binding to an immunoglobulin; a fusion protein of the peptide; nucleic acids encoding the peptide and the fusion protein, respectively; production methods for the peptide and the fusion protein, respectively; a composition and a means for binding an immunoglobulin; a pharmaceutical composition for the treatment or prevention of a disease induced by the binding between C1q and an immunoglobulin, which comprises a peptide capable of binding to the immunoglobulin or a fusion protein of the peptide; and others.

11 Claims, 6 Drawing Sheets

SEQUENCE LISTING

```
<160> NUMBER OF SEQ ID NOS: 27

<210> SEQ ID NO 1
<211> LENGTH: 6
<212> TYPE: PRT
<213> ORGANISM: Artificial Sequence
<220> FEATURE:
<223> OTHER INFORMATION: Immunoglobulin binding peptide

<400> SEQUENCE: 1

Pro Gly Leu Tyr Tyr Phe
1               5


<210> SEQ ID NO 2
<211> LENGTH: 9
<212> TYPE: PRT
<213> ORGANISM: Artificial Sequence
<220> FEATURE:
<223> OTHER INFORMATION: Immunoglobulin binding peptide

<400> SEQUENCE: 2

Cys Lys Val Pro Gly Leu Tyr Tyr Phe
1               5


<210> SEQ ID NO 3
<211> LENGTH: 15
<212> TYPE: PRT
<213> ORGANISM: Artificial Sequence
<220> FEATURE:
<223> OTHER INFORMATION: Immunoglobulin binding peptide

<400> SEQUENCE: 3

Ser Gly Lys Phe Thr Cys Lys Val Pro Gly Leu Tyr Tyr Phe Thr
1               5                   10                  15


<210> SEQ ID NO 4
<211> LENGTH: 15
<212> TYPE: PRT
<213> ORGANISM: Artificial Sequence
<220> FEATURE:
<223> OTHER INFORMATION: Immunoglobulin binding peptide

<400> SEQUENCE: 4
```

-continued

Phe Thr Cys Lys Val Pro Gly Leu Tyr Tyr Phe Thr Tyr His Ala
1 5 10 15

<210> SEQ ID NO 5
<211> LENGTH: 15
<212> TYPE: PRT
<213> ORGANISM: Artificial Sequence
<220> FEATURE:
<223> OTHER INFORMATION: Immunoglobulin binding peptide

<400> SEQUENCE: 5

Ser Thr Gly Lys Phe Thr Cys Lys Val Pro Gly Leu Tyr Tyr Phe
1 5 10 15

<210> SEQ ID NO 6
<211> LENGTH: 15
<212> TYPE: PRT
<213> ORGANISM: Artificial Sequence
<220> FEATURE:
<223> OTHER INFORMATION: Immunoglobulin binding peptide

<400> SEQUENCE: 6

Lys Phe Thr Cys Lys Val Pro Gly Leu Tyr Tyr Phe Val Tyr His
1 5 10 15

<210> SEQ ID NO 7
<211> LENGTH: 15
<212> TYPE: PRT
<213> ORGANISM: Artificial Sequence
<220> FEATURE:
<223> OTHER INFORMATION: Immunoglobulin binding peptide

<400> SEQUENCE: 7

Cys Lys Val Pro Gly Leu Tyr Tyr Phe Val Tyr His Ala Ser His
1 5 10 15

<210> SEQ ID NO 8
<211> LENGTH: 18
<212> TYPE: DNA
<213> ORGANISM: Homo sapiens

<400> SEQUENCE: 8
cccggtctct actacttc 18

<210> SEQ ID NO 9
<211> LENGTH: 18
<212> TYPE: DNA
<213> ORGANISM: Homo sapiens

<400> SEQUENCE: 9
cccggcctct actacttt 18

<210> SEQ ID NO 10
<211> LENGTH: 27
<212> TYPE: DNA
<213> ORGANISM: Homo sapiens

<400> SEQUENCE: 10
tgcaaggtgc ccggtctcta ctacttc 27

<210> SEQ ID NO 11
<211> LENGTH: 27
<212> TYPE: DNA
<213> ORGANISM: Homo sapiens

<400> SEQUENCE: 11

-continued tgcaaagtcc ccggcctcta ctacttt 27

<210> SEQ ID NO 12
<211> LENGTH: 45
<212> TYPE: DNA
<213> ORGANISM: Homo sapiens

<400> SEQUENCE: 12
agtggcaagt tcacctgcaa ggtgcccggt ctctactact tcacc 45

<210> SEQ ID NO 13
<211> LENGTH: 45
<212> TYPE: DNA
<213> ORGANISM: Homo sapiens

<400> SEQUENCE: 13
ttcacctgca aggtgcccgg tctctactac ttcacctacc acgcc 45

<210> SEQ ID NO 14
<211> LENGTH: 45
<212> TYPE: DNA
<213> ORGANISM: Homo sapiens

<400> SEQUENCE: 14
agcactggca agttcacctg caaagtcccc ggcctctact acttt 45

<210> SEQ ID NO 15
<211> LENGTH: 45
<212> TYPE: DNA
<213> ORGANISM: Homo sapiens

<400> SEQUENCE: 15
aagttcacct gcaaagtccc cggcctctac tactttgtct accac 45

<210> SEQ ID NO 16
<211> LENGTH: 45
<212> TYPE: DNA
<213> ORGANISM: Homo sapiens

<400> SEQUENCE: 16
tgcaaagtcc ccggcctcta ctactttgtc taccacgcgt cgcat 45

<210> SEQ ID NO 17
<211> LENGTH: 245
<212> TYPE: PRT
<213> ORGANISM: Homo sapiens

<400> SEQUENCE: 17

```
Met Glu Gly Pro Arg Gly Trp Leu Val Leu Cys Val Leu Ala Ile Ser
1               5                   10                  15

Leu Ala Ser Met Val Thr Glu Asp Leu Cys Arg Ala Pro Asp Gly Lys
            20                  25                  30

Lys Gly Glu Ala Gly Arg Pro Gly Arg Arg Gly Arg Pro Gly Leu Lys
        35                  40                  45

Gly Glu Gln Gly Glu Pro Gly Ala Pro Gly Ile Arg Thr Gly Ile Gln
    50                  55                  60

Gly Leu Lys Gly Asp Gln Gly Glu Pro Gly Pro Ser Gly Asn Pro Gly
65                  70                  75                  80

Lys Val Gly Tyr Pro Gly Pro Ser Gly Pro Leu Gly Ala Arg Gly Ile
                85                  90                  95

Pro Gly Ile Lys Gly Thr Lys Gly Ser Pro Gly Asn Ile Lys Asp Gln
            100                 105                 110
```

```
Pro Arg Pro Ala Phe Ser Ala Ile Arg Arg Asn Pro Pro Met Gly Gly
        115                 120                 125

Asn Val Val Ile Phe Asp Thr Val Ile Thr Asn Gln Glu Glu Pro Tyr
    130                 135                 140

Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175

Ser Ser Ser Arg Gly Gln Val Arg Arg Ser Leu Gly Phe Cys Asp Thr
            180                 185                 190

Thr Asn Lys Gly Leu Phe Gln Val Val Ser Gly Gly Met Val Leu Gln
        195                 200                 205

Leu Gln Gln Gly Asp Gln Val Trp Val Glu Lys Asp Pro Lys Lys Gly
    210                 215                 220

His Ile Tyr Gln Gly Ser Glu Ala Asp Ser Val Phe Ser Gly Phe Leu
225                 230                 235                 240

Ile Phe Pro Ser Ala
                245


<210> SEQ ID NO 18
<211> LENGTH: 253
<212> TYPE: PRT
<213> ORGANISM: Homo sapiens

<400> SEQUENCE: 18

Met Met Met Lys Ile Pro Trp Gly Ser Ile Pro Val Leu Met Leu Leu
1               5                   10                  15

Leu Leu Leu Gly Leu Ile Asp Ile Ser Gln Ala Gln Leu Ser Cys Thr
            20                  25                  30

Gly Pro Pro Ala Ile Pro Gly Ile Pro Gly Ile Pro Gly Thr Pro Gly
        35                  40                  45

Pro Asp Gly Gln Pro Gly Thr Pro Gly Ile Lys Gly Glu Lys Gly Leu
    50                  55                  60

Pro Gly Leu Ala Gly Asp His Gly Glu Phe Gly Glu Lys Gly Asp Pro
65                  70                  75                  80

Gly Ile Pro Gly Asn Pro Gly Lys Val Gly Pro Lys Gly Pro Met Gly
                85                  90                  95

Pro Lys Gly Gly Pro Gly Ala Pro Gly Ala Pro Gly Pro Lys Gly Glu
            100                 105                 110

Ser Gly Asp Tyr Lys Ala Thr Gln Lys Ile Ala Phe Ser Ala Thr Arg
        115                 120                 125

Thr Ile Asn Val Pro Leu Arg Arg Asp Gln Thr Ile Arg Phe Asp His
    130                 135                 140

Val Ile Thr Asn Met Asn Asn Asn Tyr Glu Pro Arg Ser Gly Lys Phe
145                 150                 155                 160

Thr Cys Lys Val Pro Gly Leu Tyr Tyr Phe Thr Tyr His Ala Ser Ser
                165                 170                 175

Arg Gly Asn Leu Cys Val Asn Leu Met Arg Gly Arg Glu Arg Ala Gln
            180                 185                 190

Lys Val Val Thr Phe Cys Asp Tyr Ala Tyr Asn Thr Phe Gln Val Thr
        195                 200                 205

Thr Gly Gly Met Val Leu Lys Leu Glu Gln Gly Glu Asn Val Phe Leu
    210                 215                 220

Gln Ala Thr Asp Lys Asn Ser Leu Leu Gly Met Glu Gly Ala Asn Ser
225                 230                 235                 240
```

```
Ile Phe Ser Gly Phe Leu Leu Phe Pro Asp Met Glu Ala
                245                 250


<210> SEQ ID NO 19
<211> LENGTH: 245
<212> TYPE: PRT
<213> ORGANISM: Homo sapiens

<400> SEQUENCE: 19

Met Asp Val Gly Pro Ser Ser Leu Pro His Leu Gly Leu Lys Leu Leu
1               5                   10                  15

Leu Leu Leu Leu Leu Leu Pro Leu Arg Gly Gln Ala Asn Thr Gly Cys
            20                  25                  30

Tyr Gly Ile Pro Gly Met Pro Gly Leu Pro Gly Ala Pro Gly Lys Asp
        35                  40                  45

Gly Tyr Asp Gly Leu Pro Gly Pro Lys Gly Glu Pro Gly Ile Pro Ala
    50                  55                  60

Ile Pro Gly Ile Arg Gly Pro Lys Gly Gln Lys Gly Glu Pro Gly Leu
65                  70                  75                  80

Pro Gly His Pro Gly Lys Asn Gly Pro Met Gly Pro Pro Gly Met Pro
                85                  90                  95

Gly Val Pro Gly Pro Met Gly Ile Pro Gly Glu Pro Gly Glu Glu Gly
            100                 105                 110

Arg Tyr Lys Gln Lys Phe Gln Ser Val Phe Thr Val Thr Arg Gln Thr
        115                 120                 125

His Gln Pro Pro Ala Pro Asn Ser Leu Ile Arg Phe Asn Ala Val Leu
    130                 135                 140

Thr Asn Pro Gln Gly Asp Tyr Asp Thr Ser Thr Gly Lys Phe Thr Cys
145                 150                 155                 160

Lys Val Pro Gly Leu Tyr Tyr Phe Val Tyr His Ala Ser His Thr Ala
                165                 170                 175

Asn Leu Cys Val Leu Leu Tyr Arg Ser Gly Val Lys Val Val Thr Phe
            180                 185                 190

Cys Gly His Thr Ser Lys Thr Asn Gln Val Asn Ser Gly Gly Val Leu
        195                 200                 205

Leu Arg Leu Gln Val Gly Glu Glu Val Trp Leu Ala Val Asn Asp Tyr
    210                 215                 220

Tyr Asp Met Val Gly Ile Gln Gly Ser Asp Ser Val Phe Ser Gly Phe
225                 230                 235                 240

Leu Leu Phe Pro Asp
                245


<210> SEQ ID NO 20
<211> LENGTH: 738
<212> TYPE: DNA
<213> ORGANISM: Homo sapiens

<400> SEQUENCE: 20

atggagggtc cccggggatg gctggtgctc tgtgtgctgg ccatatcgct ggcctctatg      60

gtgaccgagg acttgtgccg agcaccagac gggaagaaag gggaggcagg aagacctggc     120

agacgggggc ggccaggcct caagggggag caaggggagc cgggggcccc tggcatccgg     180

acaggcatcc aaggccttaa aggagaccag ggggaacctg ggccctctgg aaaccccggc     240

aaggtgggct acccagggcc cagcggcccc ctcggagccc gtggcatccc gggaattaaa     300

ggcaccaagg gcagcccagg aaacatcaag gaccagccga ggccagcctt ctccgccatt     360
```

-continued

```
cggcggaacc ccccaatggg gggcaacgtg gtcatcttcg acacggtcat caccaaccag    420

gaagaaccgt accagaacca ctccggccga ttcgtctgca ctgtacccgg ctactactac    480

ttcaccttcc aggtgctgtc ccagtgggaa atctgcctgt ccatcgtctc ctcctcaagg    540

ggccaggtcc gacgctccct gggcttctgt gacaccacca acaaggggct cttccaggtg    600

gtgtcagggg gcatggtgct tcagctgcag cagggtgacc aggtctgggt tgaaaaagac    660

cccaaaaagg gtcacattta ccagggctct gaggccgaca gcgtcttcag cggcttcctc    720

atcttcccat ctgcctga                                                  738
```

<210> SEQ ID NO 21
<211> LENGTH: 762
<212> TYPE: DNA
<213> ORGANISM: Homo sapiens

<400> SEQUENCE: 21

```
atgatgatga agatcccatg ggcagcatc ccagtactga tgttgctcct gctcctgggc     60

ctaatcgata tctcccaggc ccagctcagc tgcaccgggc ccccagccat ccctggcatc    120

ccgggtatcc ctgggacacc tggccccgat ggccaacctg ggaccccagg gataaaagga    180

gagaaagggc ttccagggct ggctggagac catggtgagt tcggagagaa gggagaccca    240

gggattcctg ggaatccagg aaaagtcggc cccaagggcc ccatgggccc taaaggtggc    300

ccaggggccc ctggagcccc aggccccaaa ggtgaatcgg gagactacaa ggccacccag    360

aaaatcgcct tctctgccac aagaaccatc aacgtccccc tgcgccggga ccagaccatc    420

cgcttcgacc acgtgatcac caacatgaac aacaattatg agccccgcag tggcaagttc    480

acctgcaagg tgcccggtct ctactacttc acctaccacg ccagctctcg agggaacctg    540

tgcgtgaacc tcatgcgtgg ccgggagcgt gcacagaagg tggtcacctt ctgtgactat    600

gcctacaaca ccttccaggt caccaccggt ggcatggtcc tcaagctgga gcagggggag    660

aacgtcttcc tgcaggccac cgacaagaac tcactactgg gcatggaggg tgccaacagc    720

atcttttccg ggttcctgct ctttccagat atggaggcct ga                       762
```

<210> SEQ ID NO 22
<211> LENGTH: 738
<212> TYPE: DNA
<213> ORGANISM: Homo sapiens

<400> SEQUENCE: 22

```
atggacgtgg ggcccagctc cctgccccac cttgggctga agctgctgct gctcctgctg     60

ctgctgcccc tcaggggcca agccaacaca ggctgctacg ggatcccagg gatgcccggc    120

ctgcctgggg caccagggaa ggatgggtac gacggactgc cggggcccaa gggggagcca    180

ggaatcccag ccattcccgg gatccgagga cccaaagggc agaagggaga acccggctta    240

cccggccatc ctgggaaaaa tggccccatg ggaccccctg ggatgccagg ggtgcccggc    300

cccatgggca tccctggaga gccaggtgag gagggcagat acaagcagaa attccagtca    360

gtgttcacgg tcactcggca gacccaccag ccccctgcac ccaacagcct gatcagattc    420

aacgcggtcc tcaccaaccc gcagggagat tatgacacga gcactggcaa gttcacctgc    480

aaagtccccg gcctctacta ctttgtctac cacgcgtcgc atacagccaa cctgtgcgtg    540

ctgctgtacc gcagcggcgt caaagtggtc accttctgtg gccacacgtc caaaaccaat    600

caggtcaact cgggcggtgt gctgctgagg ttgcaggtgg gcgaggaggt gtggctggct    660

gtcaatgact actacgacat ggtgggcatc cagggctctg acagcgtctt ctccggcttc    720
```

-continued

```
ctgctcttcc ccgactag                                                    738


<210> SEQ ID NO 23
<211> LENGTH: 6
<212> TYPE: PRT
<213> ORGANISM: Artificial Sequence
<220> FEATURE:
<223> OTHER INFORMATION: Immunoglobulin binding peptide

<400> SEQUENCE: 23

Pro Gly Ala Tyr Tyr Phe
1               5


<210> SEQ ID NO 24
<211> LENGTH: 6
<212> TYPE: PRT
<213> ORGANISM: Artificial Sequence
<220> FEATURE:
<223> OTHER INFORMATION: Immunoglobulin binding peptide

<400> SEQUENCE: 24

Pro Gly Leu Ala Tyr Phe
1               5


<210> SEQ ID NO 25
<211> LENGTH: 6
<212> TYPE: PRT
<213> ORGANISM: Artificial Sequence
<220> FEATURE:
<223> OTHER INFORMATION: Immunoglobulin binding peptide

<400> SEQUENCE: 25

Pro Gly Leu Tyr Ala Phe
1               5


<210> SEQ ID NO 26
<211> LENGTH: 9
<212> TYPE: PRT
<213> ORGANISM: Artificial Sequence
<220> FEATURE:
<223> OTHER INFORMATION: Immunoglobulin binding peptide

<400> SEQUENCE: 26

Cys Lys Ala Pro Gly Leu Tyr Tyr Phe
1               5


<210> SEQ ID NO 27
<211> LENGTH: 15
<212> TYPE: PRT
<213> ORGANISM: Artificial Sequence
<220> FEATURE:
<223> OTHER INFORMATION: Immunoglobulin binding peptide

<400> SEQUENCE: 27

Ser Thr Ala Lys Phe Thr Cys Lys Val Pro Gly Leu Tyr Tyr Phe
1               5                   10                  15
```

PEPTIDE CAPABLE OF BINDING TO IMMUNOGLOBULIN

This application is a U.S. national stage of International Application No. PCT/JP2008/064837 filed Aug. 20, 2008.

TECHNICAL FIELD

The present invention relates to a peptide capable of binding to an immunoglobulin, a fusion protein of the peptide, nucleic acids encoding the peptide and the fusion protein, production methods for the peptide and the fusion protein, composition and means for binding an immunoglobulin. The present invention also relates to a pharmaceutical composition for the treatment or prevention of a disease induced by the binding between C1q and an immunoglobulin, which comprises a peptide capable of binding to the immunoglobulin or a fusion protein of the peptide, and others.

BACKGROUND ART

C1q is one of the complement proteins, and is known to act in the complement activation pathways. For instance, the activation of the classical pathway is known to be triggered by binding of C1q to the Fc fragment of an immunoglobulin molecule.

It has been reported that rheumatoid arthritis (RA) patients with large quantities of blood concentration of C1q will suffer from joint destruction in the future (Non-patent Document 1). Since the activation of C1q described above is thought to be involved, development of an inhibitor of the binding between C1q and the immunoglobulin molecule is needed.

The possibility that an arginine residue on the C1q B subunit (B chain) was involved in the binding between C1q and immunoglobulin molecules has been reported (Non-patent Document 2). However, as this report was based on a prediction by a computer simulation, the actual immunoglobulin binding site was not clear. In addition, there was no detailed amino acid sequence of the binding site.

Proteins such as Protein A or Protein G, which can specifically bind to immunoglobulins, are used in the purification of immunoglobulins. However, since these proteins bind strongly to immunoglobulins, once they are bound, a harsh condition such as using a strongly acidic buffer is required for separation. For this reason, the conformation of the immunoglobulin is prone to be unfolded, and a high-affinity antibody cannot be purified.

Non-patent Document 1: Ochi T et al., Arthritis Rheum. 1988 January; 31(1): 37-73

Non-patent Document 2: Gaboriaud C et al., J Biol Chem. 2003 Nov. 21; 278(47): 46974-82. Epub 2003 Sep. 5

DISCLOSURE OF THE INVENTION

Problems to be Solved by the Invention

It is an object of the present invention to provide a peptide capable of binding to an immunoglobulin, a fusion protein of the peptide, nucleic acids encoding the peptide and the fusion protein, vectors comprising such nucleic acids, and others. In addition, it is also an object of the present invention to provide a novel antibody purification method allowing an antibody having a high affinity for the antigen without unfolding the conformation of the antibody, and a composition and means therefor.

Means for Solving the Problems

In view of the above situation, the present inventors carried out earnest studies, and as a result, successfully identified the amino acid sequence involved in the binding between C1q and an immunoglobulin to reach completion of the present invention. In addition, the amino acid sequence surprisingly did not contain the arginine residue reported to be involved in the binding. In addition, since the peptide comprising this amino acid sequence can bind to an immunoglobulin more weakly than Protein A and Protein G, it solves problems caused by conventional antibody purification such as unfolding of the conformation of the antibody and limitations on the antibody targeted for purification (such as inability to purify antibodies with high affinity to the antigen), and enables antibody purification under a mild condition.

That is to say, the present invention relates to (1) a peptide capable of binding to an immunoglobulin, selected from the group consisting of:

(a) a peptide having any of the amino acid sequences of SEQ ID NO: 1 to 7;

(b) a peptide having an amino acid sequence resulting from the deletion, substitution or addition of one or several amino acids in any of the amino acid sequences of SEQ ID NO: 1 to 7; and (c) a peptide having an amino acid sequence with 66.7% or greater homology to any of the amino acid sequences of SEQ ID NO: 1 to 7, (2) the peptide according to (1), having any of the amino acid sequences of SEQ ID NO: 1 to 7, (3) the peptide according to (1) or (2), having the amino acid sequence of SEQ ID NO: 1, (4) a nucleic acid encoding a peptide capable of binding to an immunoglobulin, selected from the group consisting of:

(a) a nucleic acid encoding the peptide according to (1);

(b) a nucleic acid having any of the nucleotide sequences of SEQ ID NO: 8 to 16;

(c) a nucleic acid having a nucleotide sequence resulting from the deletion, substitution or addition of one or several nucleotides in any of the nucleotide sequences of SEQ ID NO: 8 to 16;

(d) a nucleic acid that may hybridize with the nucleic acid of (b) or (c), or the complementary strand thereof under a stringent condition; and (e) a nucleic acid having a nucleotide sequence with 50% or greater homology to any of the nucleotide sequences of SEQ ID NO: 8 to 16, (5) the nucleic acid according to (4), having any of the nucleotide sequences of SEQ ID NO: 8 to 16, (6) the nucleic acid according to (4) or (5), having the nucleotide sequence of SEQ ID NO: 8 or 9, (7) a vector comprising the nucleic acid according to any one of (4) to (6), (8) a fusion protein, in which the peptide according to any one of (1) to (3) is added to the N-terminus and/or C-terminus of a target protein, (9) a nucleic acid encoding the fusion protein according to (8),

(10) a vector comprising the nucleic acid according to (9),

(11) a cell comprising the nucleic acid according to any one of (4) to (6) or (9), or the vector according to (7) or (10),

(12) a method for producing a peptide capable of binding to an immunoglobulin, comprising the steps of:

(a) transforming a cell with the vector according to (7); and (b) culturing the cell to produce the peptide,

(13) a peptide capable of binding to an immunoglobulin, which can be obtained by the method according to (12),

(14) a method for producing a fusion protein in which a peptide capable of binding to an immunoglobulin is added to the N-terminus and/or C-terminus of a target protein, comprising the steps of:
(a) transforming a cell with the vector according to (10); and
(b) culturing the cell to produce the fusion protein,
(15) the method according to (14), further comprising the step of obtaining the target protein from the fusion protein,
(16) a fusion protein which can be obtained by the method according to (14) or (15),
(17) a composition for binding an immunoglobulin, comprising the peptide according to any one of (1) to (3) or the fusion protein according to (8),
(18) the composition according to (17), which is used for determining the presence or the amount of an immunoglobulin, or for isolating an immunoglobulin,
(19) a means for binding an immunoglobulin on which the peptide according to any one of (1) to (3) or the fusion protein according to (8) is immobilized,
(20) the means according to (19), which is used for determining the presence or the amount of an immunoglobulin, or for isolating an immunoglobulin,
(21) a method for binding an immunoglobulin, comprising:
(a) adding to a sample the peptide according to any one of (1) to (3) or the fusion protein according to (8); and
(b) checking for a complex of the peptide or fusion protein and an immunoglobulin,
(22) a kit for use in the method according to (21), containing a peptide capable of binding to an immunoglobulin or a fusion protein containing the peptide,
(23) a pharmaceutical composition for the treatment or prevention of a disease induced by the binding between C1q and an immunoglobulin, the pharmaceutical composition comprising the peptide according to any one of (1) to (3) or the fusion protein according to (8),
(24) the pharmaceutical composition according to (23), wherein the disease is rheumatoid arthritis,
(25) the pharmaceutical composition according to (23), wherein the disease is an immune-complex disease such as systemic lupus erythematosus (SLE), glomerulonephritis, vasculitis or arthritis,
(26) the peptide according to any one claim among (1) to (3) or the fusion protein according to (8), which is labeled, and
(27) a method for detecting an antibody in a sample, comprising reacting the labeled peptide or fusion protein according to (26) with an antibody in a sample, and then detecting the peptide or the fusion protein bound to the antibody.

Effect of the Invention

According to the present invention, the followings are provided; a peptide capable of binding to an immunoglobulin, a fusion protein of the peptide, nucleic acids encoding the peptide and the fusion protein, production methods for the peptide and the fusion protein, a composition and means for binding an immunoglobulin, and pharmaceutical composition for the treatment or prevention of a disease induced by the binding between C1q and an immunoglobulin, which comprises the peptide capable of binding to the immunoglobulin or the fusion protein of the peptide, and others.

BEST MODE FOR CARRYING OUT THE INVENTION

Figure 1:
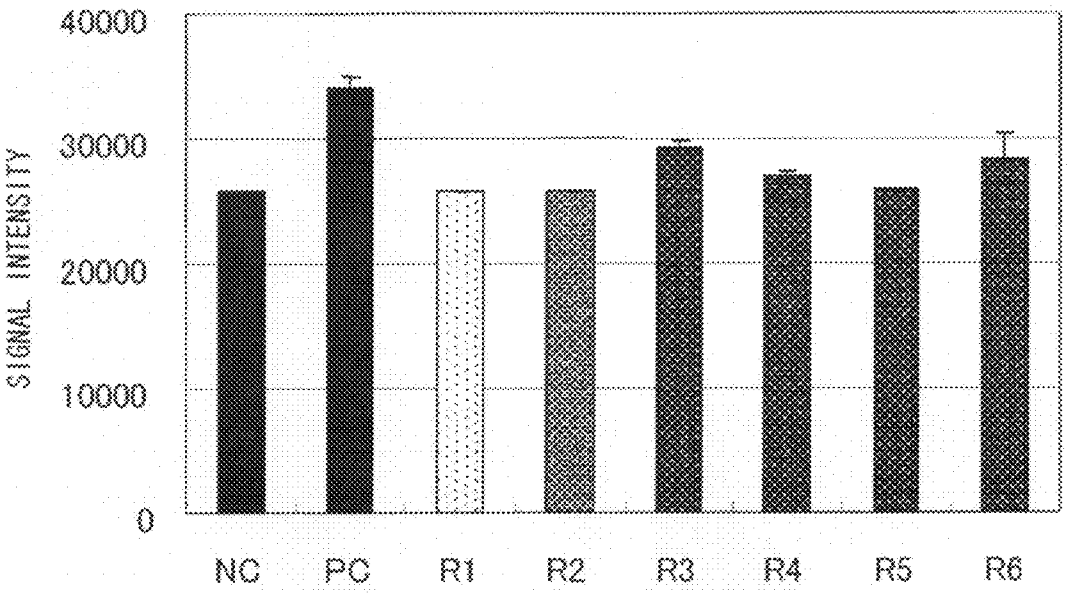
FIG. 1 shows that peptide R1 having 6 amino acids, peptide R2 having 9 amino acids and peptides R3 to R6 having 15 amino acids inhibit the binding between C1q and an immunoglobulin. In this figure, NC is the result for a sample in which peptide-free DMSO was added to a reaction solution not containing alkaline phosphatase (ALP)-labeled human immunoglobulin (IgG), and PC is the result for a sample in which peptide-free DMSO was added to a reaction solution containing alkaline phosphatase (ALP)-labeled human immunoglobulin (IgG).

In one aspect, the present invention relates to a peptide capable of binding to an immunoglobulin, selected from the group consisting of:

(a) a peptide having any of the amino acid sequences of SEQ ID NO: 1 to 7;

(b) a peptide having an amino acid sequence resulting from the deletion, substitution or addition of one or several amino acids in any of the amino acid sequences of SEQ ID NO: 1 to 7; and (c) a peptide having an amino acid sequence with 66.7% or greater homology to any of the amino acid sequences of SEQ ID NO: 1 to 7. The peptide of the present invention has a low affinity to an immunoglobulin compared to Protein A and Protein G, for which reason, for instance, dissociation of an immunoglobulin bound to the peptide of the present invention under a mild condition, or the like, is allowed. In addition, denaturation of the immunoglobulin per se bound to the peptide of the present invention is also reduced. The affinity can be evaluated by known methods in the relevant technical field. For instance, the peptide may be incubated in the presence of immunoglobulin to check directly whether or not there is binding.

The peptide of the present invention is capable of binding to immunoglobulin. The above peptide is a peptide having any of the amino acid sequences of SEQ ID NO: 1 to 7, a peptide having an amino acid sequence resulting from the deletion, substitution or addition of one or more, preferably, one or several, for instance, 2, 3, 4, 5, 6, 7, 8, 9, 10, 11, 12, 13, or 14 amino acids in any of the amino acid sequences of SEQ ID NO: 1 to 7 (mutant peptide), and a peptide having an amino acid sequence with, for instance, 26.6% or greater or 44.4% or greater, preferably at least 50% or greater, and more preferably, for instance, 60, 66.7, 70, 75, 80, 83.3, 85, 90, 93% or greater homology to any of the amino acid sequences of SEQ ID NO: 1 to 7. Amino acid sequence homology can be calculated using, for instance, FASTA, BLAST, DNASIS (manufactured by Hitachi Software Engineering Co., Ltd.), or GENETYX (manufactured by Genetyx Corporation). Alternatively, in the case of a short chain peptide, it can also be calculated by simply comparing the sequences. In addition, any of these amino acids may be modified suitably. Regardless of which amino acid sequence the peptide has, the peptide of the present invention is capable of binding to an immunoglobulin.

The peptide of the present invention may be any one as long as it is one having the above amino acid sequence. For instance, it may be the peptide itself consisting of an amino acid sequence shown in any of SEQ ID NO: 1 to 7 itself, or it may comprise the above amino acid sequence or its homologous sequence as a core sequence and have a variety of substances such as peptides or amino acids, analogs thereof, polyethyleneglycol, sugars, polysaccharides or nucleotides added to the N-terminus and/or C-terminus of the amino acid sequence. Substances such as fluorescent label, biotin, streptavidin, digoxigenin (DIG), magnetic beads, latex beads or gold colloid may be added to the N/C-terminus via an amino acid or a peptide. For instance, when a peptide is added, such a peptide may be the one comprising 1 to 50, for instance, 1 to 20, 1 to 15 or 1 to 9 amino acids. In addition, such a peptide may be the one having a function such as, functioning as a histidine-tag, a GST-tag, an S-tag, a Myc-tag, an HA-tag or an E-tag.

The peptide of the present invention can be produced and obtained by various methods known to those skilled in the art. For instance, it may be produced by a genetic engineering way based on the nucleotide sequence encoding the peptide of the present invention. Since the peptide of the present invention is capable of binding to an immunoglobulin as described above, by using such a peptide to bind an immunoglobulin, determination of the presence or the amount of an immunoglobulin, isolation of an immunoglobulin, and the like, are possible.

In another aspect, the present invention relates to a nucleic acid encoding a peptide capable of binding to an immunoglobulin, selected from the group consisting of:

(a) a nucleic acid encoding the peptide described above;

(b) a nucleic acid having any of the nucleotide sequences of SEQ ID NO: 8 to 16;

(c) a nucleic acid having a nucleotide sequence resulting from the deletion, substitution or addition of one or several nucleotides in any of the nucleotide sequences of SEQ ID NO: 8 to 16;

(d) a nucleic acid that may hybridize with the nucleic acid of (b) or (c), or the complementary strand thereof under a stringent condition; and (e) a nucleic acid having a nucleotide sequence with 50% or greater homology to any of the nucleotide sequences of SEQ ID NO: 8 to 16. Herein, a nucleic acid means a single-stranded or a double-stranded DNA or RNA. The nucleic acid of the present invention may be produced and obtained by various methods known to those skilled in the art. In the present invention, the nucleotide sequences of SEQ ID NO: 8, 10, 12 and 13 are derived from the C1q B subunit and encode respectively the amino acid sequences of SEQ ID NO: 1, 2, 3 and 4. Similarly, the nucleotide sequences of SEQ ID NO: 9, 11 and 14 to 16 are derived from the C1q C subunit and encode respectively the amino acid sequences of SEQ ID NO: 1, 2, 5 and 6.

Specifically, the nucleic acid of the present invention is (1) a nucleic acid encoding a peptide having any of the amino acid sequences of SEQ ID NO: 1 to 7, (2) a nucleic acid encoding a peptide having an amino acid sequence resulting from the deletion, substitution or addition of one or more, preferably, one or several, for instance, on the order of 2, 3, 4, 5, 6, 7, 8, 9, 10, 11, 12, 13 or 14 amino acids in any of the amino acid sequences of SEQ ID NO: 1 to 7, (3) a nucleic acid encoding a peptide having an amino acid sequence with, for instance, 26.6% or greater or 44.4% or greater, preferably, at least 50% or greater, more preferably, for instance, 60, 66.7, 70, 75, 80, 83.3, 85, 90 or 93% or greater homology to any of the amino acid sequences of SEQ ID NO: 1 to 7, (4) a nucleic acid having any of the nucleotide sequences of SEQ ID NO: 8 to 16, (5) a nucleic acid having a nucleotide sequence resulting from the deletion, substitution or addition of one or more, preferably, one or several, for instance, on the order of 2, 3, 4, 5, 6, 7, 8 or 9 nucleotides in any of the nucleotide sequences of SEQ ID NO: 8 to 16, (6) a nucleic acid that may hybridize under a stringent condition with any of the nucleic acids described above in (3) or (4) or the complementary strand thereof, and (7) a nucleic acid having a nucleotide sequence with at least 50% or greater, preferably, for instance, 60, 70, 75, 80, 90, 93, 95 or 97% or greater homology to any of the nucleotide sequences of SEQ ID NO: 8 to 16, and others. In addition, any of these nucleotides may be modified properly. Regardless of which nucleotide sequence the nucleic acid has, the nucleic acid of the present invention may encode a peptide capable of binding to an immunoglobulin.

As the stringent condition mentioned above, for instance, conditions such as those described in J. Sambrook et al., "Molecular Cloning: A Laboratory Manual, Second Edition", 1989, Cold Spring Harbor Laboratory Press may be included. For instance, following hybridization with a probe at 68° C. in a solution containing 6×SSC, 5×Denhardt's solution, 0.5% SDS and 100 μg/ml denatured salmon sperm DNA, the condition of changing the washing condition from room temperature in 2×SSC, 0.1% SDS to 68° C. in 0.1×SSC, 0.5% SDS; the condition of twice 15 minutes in a solution containing 2×SSPE (described in Frederick M. Ausubel et al., "Current Protocols in Molecular Biology", 1987, John Wiley & Sons, Hoboken N.J.) and 0.1% SDS, further twice 15 minutes in a solution containing 0.5×SSPE and 0.1% SDS, and then twice 15 minutes in a solution containing 0.1×SSPE and 0.1% SDS at 65° C.; or the condition of twice 15 minutes in a solution containing 2×SSPE, 0.1% SDS and formamide (5 to 50%), further twice 15 minutes in a solution containing 0.5×SSPE, 0.1% SDS and formamide (5 to 50%), and then twice 15 minutes in a solution containing 0.1×SSPE, 0.1% SDS and formamide (5 to 50%) at 65° C., and others.

The above-mentioned nucleotide sequence homology can be calculated using, for instance, FASTA, BLAST, DNASIS (manufactured by Hitachi Software Engineering Co., Ltd.), or GENETYX (manufactured by Genetyx Corporation).

The nucleic acid of the present invention may be any as long as it has the above nucleotide sequence. For instance, it may be a nucleic acid consisting of any of the nucleotide sequences of SEQ ID NO: 8 to 16 per se, or it may comprise the above nucleotide sequence as a core sequence and have a variety of substances such as a nucleotide, a polynucleotide, or analogs thereof added at the 5' end and/or 3' end of the sequence. For instance, when a polynucleotide is added, such a polynucleotide may be the one comprising 1 to 150, for instance, 1 to 60, 1 to 45 or 1 to 18 nucleotides.

In an additional aspect, the present invention relates to a vector comprising the above nucleic acid. The vector of the present invention may be any as long as it comprises the above nucleic acid. The type of vector, sequences other than the nucleotide sequence of the nucleic acid described above, and the like, may be selected properly according to a variety of conditions such as the species of the host into which the vector is introduced and the purpose. The vector of the present invention, for instance, can also be used as an expression vector for a fusion protein, in which a peptide capable of binding to an immunoglobulin is added to the N-terminus or C-terminus of a target protein, by inserting in-frame a nucleotide sequence encoding a target protein at the 5' end or 3' end of the nucleotide sequence of SEQ ID NO: 8 or 9. In order to facilitate isolation of the target protein from the fusion protein, the vector of the present invention may contain a sequence recognized by a protease such as, for instance, HRV 3C, thrombin, Factor Xa or enterokinase between the above nucleotide sequence and the insertion site of the target protein nucleotide sequence. The peptide capable of binding to an immunoglobulin of the present invention described above may be obtained by introducing the vector of the present invention into a cell to produce protein.

In another aspect, the present invention relates to a fusion protein in which the peptide of the present invention capable of binding to an immunoglobulin is added to the N-terminus and/or C-terminus of a target protein. The fusion protein of the present invention can be produced and obtained by various methods known to those skilled in the art. Since the fusion protein of the present invention is the one comprising a peptide capable of binding to an immunoglobulin, such a peptide can be used as a tag sequence to isolate and/or purify a target protein, and the like. In addition, since the peptide of the present invention, as described above, has a low affinity to an immunoglobulin, the fusion protein of the present invention has advantages such as, for instance, when immobilized on a purification column, purification of immunoglobulin under a mild condition compared to Protein A or Protein G and repeated use of such a column (deterioration is inhibited) are allowed, and, for instance, when used as a probe for detecting an immunoglobulin, reprobing is facilitated.

The target protein contained in the fusion protein of the present invention may be any protein. When the fusion protein of the present invention contains as the target protein an enzyme such as, for instance, alkaline phosphatase (ALP), peroxidase (HRP), fluorescence proteins such as luciferase or green fluorescence protein (GFP), β-galactosidase, glutathione S-transferase or maltose binding protein, detection of binding between the peptide capable of binding to an immunoglobulin contained in the fusion protein of the present invention and an immunoglobulin, and the like, is facilitated. In addition the fusion protein of the present invention may contain, for instance, a tag sequence such as histidine-tag, GST-tag, S-tag, Myc-tag, HA-tag or E-tag, a nuclear localization signal, a silica binding protein, or Protein A, and others.

The fusion protein of the present invention may contain a peptide recognized by a protease between the peptide of the present invention and the target protein. Containing such a peptide allows the target protein to be isolated readily from the fusion protein.

Consequently, in an additional aspect, the present invention relates to a nucleic acid encoding the above fusion protein.

In addition, the present invention relates to a vector comprising a nucleic acid encoding the above fusion protein. The fusion protein of the present invention may be obtained by introducing such a vector into a cell to produce the protein.

In one aspect, the present invention relates to a cell comprising a nucleic acid encoding the above peptide capable of binding to an immunoglobulin, a nucleic acid encoding the above fusion protein, or a vector comprising these nucleic acids. The cell of the present invention can be produced by transforming a host cell such as, for instance, *Escherichia coli*, yeast, insect cell or animal cell, with the above nucleic acid or vector. The peptide or fusion protein of the present invention can also be produced by culturing the cell of the present invention and collecting the produced peptide capable of binding to an immunoglobulin or fusion protein containing a peptide capable of binding to an immunoglobulin.

In an additional aspect, the present invention relates to a method for producing a peptide capable of binding to an immunoglobulin, comprising the steps of:

(a) transforming a cell with a vector comprising a nucleic acid encoding a peptide capable of binding to an immunoglobulin; and (b) culturing the cell to produce the peptide.

The transformation of cell may be carried out by means and/or methods known to those skilled in the art.

Consequently, the present invention relates to a peptide capable of binding to an immunoglobulin, which can be obtained by the above peptide production method.

In another aspect, the present invention relates to a method for producing a fusion protein in which a peptide capable of binding to an immunoglobulin is added to the N-terminus and/or C-terminus of a target protein, comprising the steps of:

(a) transforming a cell with a vector comprising a nucleic acid encoding a fusion protein in which a peptide capable of binding to an immunoglobulin is added to the N-terminus or C-terminus of a target protein; and (b) culturing the cell to produce the fusion protein.

The production method for the fusion protein of the present invention may further comprise the step of obtaining the target protein from the fusion protein.

Consequently, the present invention relates to a fusion protein in which a peptide capable of binding to an immunoglobulin is added to the N-terminus and/or C-terminus of a target protein, which can be obtained by the above fusion protein production method.

In one aspect, the present invention relates to a composition for binding an immunoglobulin, comprising a peptide capable of binding to an immunoglobulin, or a fusion protein containing such a peptide. Components other than the above peptide or fusion protein may be selected suitably according to a variety of conditions such as the purpose for which the composition of the present invention is used. As described above, since the composition of the present invention contains a peptide capable of binding to an immunoglobulin, the composition of the present invention may be, for instance, a composition for determining the presence or the amount of an immunoglobulin, or a composition for isolating an immunoglobulin. According to the composition of the present invention, determination of the amount of an immunoglobulin in a sample, isolation of an immunoglobulin from a sample, and others become possible.

In another aspect, the present invention relates to a means for binding an immunoglobulin on which a peptide capable of binding to an immunoglobulin or a fusion protein containing such a peptide is immobilized. The means of the present invention is the one in which the above peptide or fusion protein is immobilized on a carrier such as, for instance, plates, resins, columns, beads, resins containing sugar such as agarose or sepharose, silica substrates, glass (slide glass and others), metal (gold and others) or apatite. Immobilization may be carried out by means/methods known to those skilled in the art such as methods via the amino group or carboxyl group of the peptide or protein, methods via the SH group of an amino acid side chain, methods by ionic interaction, and methods by hydrophobic interaction.

Since the means of the present invention, as described above, is the one on which a peptide capable of binding to an immunoglobulin is immobilized, the means of the present invention includes a means for determining the presence or the amount of an immunoglobulin and a means for isolating an immunoglobulin. The means of the present invention can also be used as, for instance, an ELISA plate, an immunoglobulin purification column, a detection glass array, a microfluidic system, an SPR sensor chip, a detection silica substrate, a pharmaceutical antibody purification system and others.

In an additional aspect, the present invention relates to a method for binding an immunoglobulin, comprising:

(a) adding to a sample a peptide capable of binding to an immunoglobulin, or a fusion protein containing such a peptide; and (b) checking for a complex of the peptide or fusion protein and an immunoglobulin.

The sample may be any as long as the sample can contain an immunoglobulin. By checking for the existence and/or amount of a complex with an immunoglobulin, it becomes possible to determine whether or not an immunoglobulin is present in the sample, and furthermore, the amount of immunoglobulin present in the sample, and the like. The peptide or fusion protein used in the method of the present invention may be the one labeled. Labels may include various ones known to those skilled in the art, such as biotinylation, fluorescence labeling, RI labeling or enzyme labeling. Adding such a label facilitates checking for a complex with a peptide or fusion protein. In addition, the method of the present invention may comprise the step of isolating an immunoglobulin from a complex.

Consequently, the present invention relates to a kit for use in a method for binding an immunoglobulin, containing a peptide capable of binding to an immunoglobulin or a fusion protein comprising such a peptide. In addition to the above peptide or fusion protein, the kit of the present invention may contain, for instance, a label, a means to check for a complex, and others.

In other aspect, the present invention relates to a pharmaceutical composition for the treatment or prevention of a disease induced by the binding between C1q and an immunoglobulin, the pharmaceutical composition comprising a peptide capable of binding to an immunoglobulin or a fusion protein comprising such a peptide. The disease induced by the binding between C1q and an immunoglobulin refers to a disease directly or indirectly resulted from such a binding, and, for instance, immune-complex diseases such as rheumatoid arthritis, arthritis, systemic lupus erythematosus (SLE), vascular inflammation group or nephritis, other inflammatory diseases, infectious diseases, or malignant tumors or others may be included. The pharmaceutical composition of the present invention can treat and prevent the above diseases by inhibiting the binding between C1q and an immunoglobulin with the contained peptide capable of binding to an immunoglobulin. Note that there is little adverse effect arising from the administration of the peptide of the present invention to a human, since the peptide of the present invention is derived from C1q, which is naturally present inside a human body, and is short with 6 to 15 residues.

In an additional aspect, the present invention relates to a method for the treatment of the prevention of a disease induced by the binding between C1q and an immunoglobulin, comprising administering to a subject an effective amount of the peptide capable of binding to an immunoglobulin or the fusion protein containing such a peptide.

Hereinafter the present invention will be described concretely and in detail showing examples; however the examples are not to be interpreted as limiting the present invention.

EXAMPLE 1

Identification of the Amino Acid Sequence in C1q, Recognized by an Immunoglobulin Materials and Methods The amino acid sequences of subunit A chain, B chain and C chain of human C1q are shown in SEQ ID NO: 17 to 19, and the nucleotide sequences in SEQ ID NO: 20 to 22. Based on the respective amino acid sequences, sequences having the amino acid sequence from each subunit with 15 amino acids (residues) at a time, shifted at intervals of three amino acids, were synthesized as synthetic peptides (sequentially, peptide No. 1 to 78, 97 to 117 and 193 to 270) on a glass array. The synthesis of each peptide was carried out at a specific location on the array to prepare a peptide array comprising synthetic peptides that encompass the entirety of the amino acid sequences of the C1q subunits. Note that the preparation of the array was outsourced to JPT.

The peptide array was coated over with 330 μl of Cy3-labeled goat anti-mouse immunoglobulin (IgG) (1 mg/ml;

manufactured by Zymed Laboratories) diluted 1,000-fold with PBS (10 mM phosphate buffer solution pH 7.0, 0.1 M NaCl), sealed and then incubated at 4° C. for 12 hours. Thereafter the array was washed once with methanol and with Milli-Q water for 5 minutes×5 times. The array slide was centrifuged and dried, and scanned with a fluorescence scanner (Agilent DNA microarray scanner; manufactured by Agilent), and the fluorescence intensity of each peptide spot on the array was quantified using a software (Feature Extraction software; manufactured by Agilent). Several spots demonstrating strong fluorescence intensities were detected. Among these, amino acid sequences of the peptide spot demonstrating fluorescence intensities that are higher than background level by 60,000 or greater (SEQ ID NO: 3 to 7) are shown in Table 1. Note that, herein, the amino acids are described by the one-letter representation, which is well known in the relevant field.

TABLE 1

| Peptide No. | Amino acid sequence | SEQ ID NO | Fluorescence intensity* |
|---|---|---|---|
| No. 149 | SGKFTCKVPGLYYFT | 3 | 65,300 |
| No. 150 | FTCKVPGLYYFTYHA | 4 | 65,311 |
| No. 244 | STGKFTCKVPGLYYF | 5 | 65,311 |
| No. 245 | KFTCKVPGLYYFVYH | 6 | 65,311 |
| No. 246 | CKVPGLYYFVYHASH | 7 | 65,313 |

*Background fluorescence intensity was 2.6

Results

Peptides No. 149 and No. 150 have sequences derived from C1q B subunit (B chain), and peptides No. 244 to No. 246 have sequences derived from C1q C subunit (C chain). From these sequences, it was predicted that the sequence required for binding between C1q and an immunoglobulin was the sequence having the 9 residues CKVPGLYYF (SEQ ID NO: 2) as a core. In addition, it was observed that in the case where the sequence contained this core sequence, binding to the immunoglobulin was not prevented by the amino acid residues added to the N-terminal or C-terminal side thereof. The nucleotide sequences of the peptides Nos. 149, 150 and 244 to 246 are shown in SEQ ID NO: 12 to 16.

EXAMPLE 2

Inhibition of the Binding Between an Immunoglobulin and C1q by a Peptide Capable of Binding to an Immunoglobulin Examination of Inhibitory Activity (1)

Materials and Methods

It was investigated whether or not the 9 residue-peptide CKVPGLYYF (SEQ ID NO: 2) considered to be necessary for the binding between C1q and an immunoglobulin (IgG) inhibits the binding between C1q and an immunoglobulin. Peptide (R2) having the amino acid sequence of SEQ ID NO: 2, peptide (R1) having a shorter amino acid sequence than this peptide, PGLYYF (SEQ ID NO: 1), as well as peptide (R3) having the amino acid sequence SGKFTCKVPGLYYFT (SEQ ID NO: 3), peptide (R4) having the amino acid sequence FTCKVPGLYYFTYHA (SEQ ID NO: 4), peptide (R5) having the amino acid sequence STGKFTCKVPGLYYF (SEQ ID NO: 5), and peptide (R6) having the amino acid sequence CKVPGLYYFVYHASH (SEQ ID NO: 7), which contain the amino acid sequence indicated by SEQ ID NO: 2, were prepared by outsourcing to GL Biochem (Shanghai). These peptides are shown in Table 2. Each peptide was dissolved in dimethylsulfoxide so as to reach a concentration of 10 mg/ml and stored.

TABLE 2

| Synthetic peptide | Amino acid sequence | SEQ ID NO |
|---|---|---|
| R1 | PGLYYF | 1 |
| R2 | CKVPGLYYF | 2 |
| R3 | SGKFTCKVPGLYYFT | 3 |
| R4 | FTCKVPGLYYFTYHA | 4 |
| R5 | STGKFTCKVPGLYYF | 5 |
| R6 | CKVPGLYYFVYHASH | 7 |

Human C1q protein (manufactured by Carbiochem) was dissolved in 10 mM HEPES, 300 mM NaCl and 40% glycerol (pH 7.2) to prepare a 200 μg/ml human C1q protein solution.

The human C1q protein solution was spotted at 2 μl (400 ng) each onto a 5 mm×15 mm size nitrocellulose membrane (Hybond C; manufactured by Amersham), which was air-dried at room temperature for approximately one hour. The nitrocellulose membrane was soaked in TBS, incubated for 5 minutes, and blocked at room temperature for one hour using TBS (20 mM Tris-HCl pH 7.5, 150 mM NaCl) containing 5% blocking agent (Amersham ECL blocking reagent; manufactured by GE Healthcare). After a slight wash in TBS, the membrane was soaked in 20 μl of a mixed solution of alkaline phosphatase (ALP)-labeled human immunoglobulin (IgG) (manufactured by BECKMAN COULTER) diluted 1000-fold in TBS and each peptide so as to reach a concentration of 500 μg/ml, and let it react at room temperature for one hour. After a slight wash in TTBS solution (TBS added with Tween 20 to a final concentration of 0.05%), the membrane was washed in the same solution for 10 minutes, shaking three times.

Detection Method Using ALP-Labeled Immunoglobulin (IgG)

After the nitrocellulose membrane was washed slightly in ALP coloring buffer (Tris-HCl containing 100 mM NaCl, 5 mM $MgCl_2$, pH 9.5), it was soaked in 30 μl ALP coloring buffer containing BCIP/NBT solution (manufactured by Promega), and colored at room temperature for 10 minutes. Upon obtaining a staining image, the nitrocellulose membrane was soaked in a sufficient amount of distilled water to wash away the coloring buffer. After washing the nitrocellulose membrane was air-dried and the staining image was captured using Multi Gauge (FUJIFILM).

Results

The results are shown in FIG. 1. From the fact that the binding was inhibited by not only peptide R2 having the 9 amino acids deemed necessary for the binding between C1q and immunoglobulin (IgG) and by peptides having this peptide as the core sequence (peptides R3 to 6), but also peptide having a shorter amino acid sequence (peptide R1), it was found that a sequence having the 6 amino acid residues PGLYYF (SEQ ID NO: 1) as a core was important for the binding between the immunoglobulin and C1q. In addition, these peptides were found to have the potential of treating or preventing a disease induced by this binding by inhibiting the binding between C1q and an immunoglobulin.

Examination of Inhibitory Activity (2)

Materials and Methods

In addition to the peptides indicated in Examination of inhibitory activity (1) of Example 2, the mutant peptides thereof were investigated as to whether or not they inhibit the binding between C1q and an immunoglobulin. The peptides shown in Table 3 were prepared by outsourcing to GL Biochem (Shanghai). Each peptide was dissolved in dimethylsulfoxide so as to reach a concentration of 10 mg/ml and stored. Note that the experiments were carried out by similar methods to Examination of inhibitory activity (1) of Example 2, and tests were also carried out for peptides R1, R2 and R5 as controls.

TABLE 3

| Synthetic peptide | Amino acid sequence | SEQ ID NO |
|---|---|---|
| R7 | PGAYYF | 23 |
| R8 | PGLAYF | 24 |
| R9 | PGLYAF | 25 |
| R10 | CKAPGLYYF | 26 |
| R11 | STAKFTCKVPGLYYF | 27 |

Results

Figure 2:
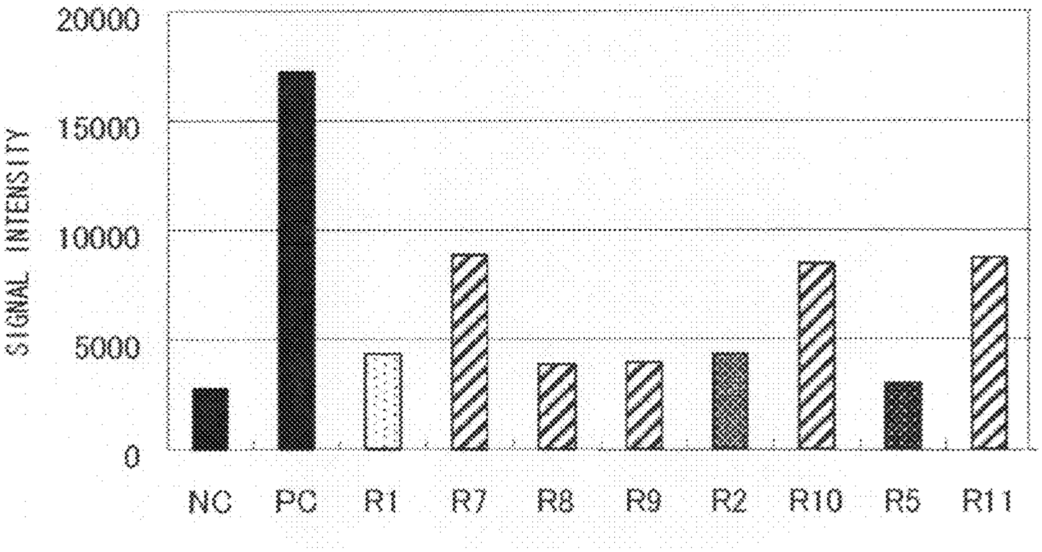
FIG. 2 shows that mutant peptides R7 to R9 having 6 amino acids, mutant peptide 10 having 9 amino acids and mutant peptide R11 having 15 amino acids inhibit the binding between C1q and an immunoglobulin. In this figure, NC is the result for a sample in which peptide-free DMSO was added to a reaction solution not containing alkaline phosphatase (ALP)-labeled human immunoglobulin (IgG), and PC is the result for a sample in which peptide-free DMSO was added to a reaction solution containing alkaline phosphatase (ALP)-labeled human immunoglobulin (IgG).

The results are shown in FIG. 2. Peptides in which a specific amino acid was substituted with alanine sufficiently inhibited the binding between C1q and an immunoglobulin. Consequently, since these mutant peptides or peptides containing these as a core also inhibit the binding between C1q and an immunoglobulin, it was found that a disease induced by this binding can be treated or prevented.

EXAMPLE 3

Study of Arthritis Inhibitory Action of a Peptide Capable of Binding to an Immunoglobulin (1) Arthritis Inhibitory Action of a Peptide Capable of Binding to an Immunoglobulin on an Arthritis-Induced Mouse-1

Materials and Methods

Using monoclonal antibody cocktail-induced arthritis mice (BALB/c Cr Slc (SPF)), the arthritis inhibitory action of the peptide indicated as R5 in Example 2 was examined. Arthritis was induced by intravenous administration of 2 mg/individual of an arthritis-inducing monoclonal antibody cocktail, followed by intraperitoneal administration of 50 μg/individual of Lipopolysaccharide (LPS) three days later. From the day following LPS administration (day 4) until day 14, 10 mg/kg of peptide. R5 was intraperitoneally administered once daily or twice daily. The positive control agent methotrexate was orally administered once daily at 0.1 mg/kg from day 4. The clinical score of the extremities was measured on even days from day 0 to day 14. Under anesthesia, blood was removed with heparin-containing physiological saline, ice-cold 4% paraformaldehyde solution was continuously injected to perfusion-fix the whole body. After perfusion-fixation subsequent, both hind limbs knee joints (the center of the femur and the center of the tibia were cut; skin and muscles were removed) and heel joints (from the center of the tibia to the toe tips) were excised and further immersion-fixed with 4% paraformaldehyde solution overnight (4° C.). Thereafter, both knee and heel joints were transferred to 50 mM PBS (4° C.), then soft x-ray radiography of the heel articulations were taken from two directions (internal side direction and upper side direction).

Preparation of Peptide Solution

Based on the animal body weight, the required amount was calculated for the peptide. A peptide solution was prepared with a 0.5% methyl cellulose solution so as to reach a concentration of 1 mg/ml, and the prepared peptide solution was stored refrigerated.

Preparation of Methotrexate Solution

Methotrexate was prepared by weighing 1 mg which was placed in an agate mortar and ground with a pestle, and then suspended by gradually adding a 0.5% methyl cellulose solution so as to reach a concentration of 0.01 mg/ml. Thereafter, the preparation was stored refrigerated.

Body Weight Measurement, General State Observation and Grouping

With the day the arthritis-inducing monoclonal antibody cocktail was administered as day 0, the animal's body weight was measured on day 0, 3, 6, 9, 12 and 14 during the test period. General state observation was performed daily.

Preparation of an Arthritis Model

To twenty 7 week-old mice, 2 mg/individual of arthritis-inducing monoclonal antibody cocktail was intravenously administered on day 0, and LPS was intraperitoneally administered at 50 μg/individual on day 3.

Administration of a Peptide Solution

The peptide solution was intraperitoneally administered at 10 mg/kg once daily (morning) or twice daily (morning and afternoon) from day 4. As a control, a 0.5% methyl cellulose solution was intraperitoneally administered once daily (morning) from day 4. For the administration a syringe needle (26G, Terumo) and a syringe barrel (1.0 ml capacity, Terumo) were used. The dosage was 10 ml/kg. Methotrexate was orally administered at 0.1 mg/kg once daily (morning) from day 4. For the administration, a peroral probe (peroral probe for mouse, Fuchigami Instruments Shop) and a syringe barrel (1.0 ml capacity, Terumo) were used. The dosage was 10 ml/kg.

Clinical Score Observation

The clinical score was observed on even days from day 0 to day 14 according to the followings. The score was 12 maximum in total for the extremities.

<Clinical Score>

0: normal articulation

1: slight inflammation and redness

2: serious erythema and swelling occupying the entirety of the limbs, interfering with the use of the limbs 3: deformation of the limbs or articulation accompanied by ankylosis, joint stiffness, loss of function Statistical Analysis Processing Method The test results were represented by mean value±standard error and the analysis was carried out using EXSAS (Version 7.1.6, Arm Systex Co., Ltd.). Wilcoxon test was carried out for the clinical score. Swelling of the legs was observed by direct visual observation.

Results

Figure 3:
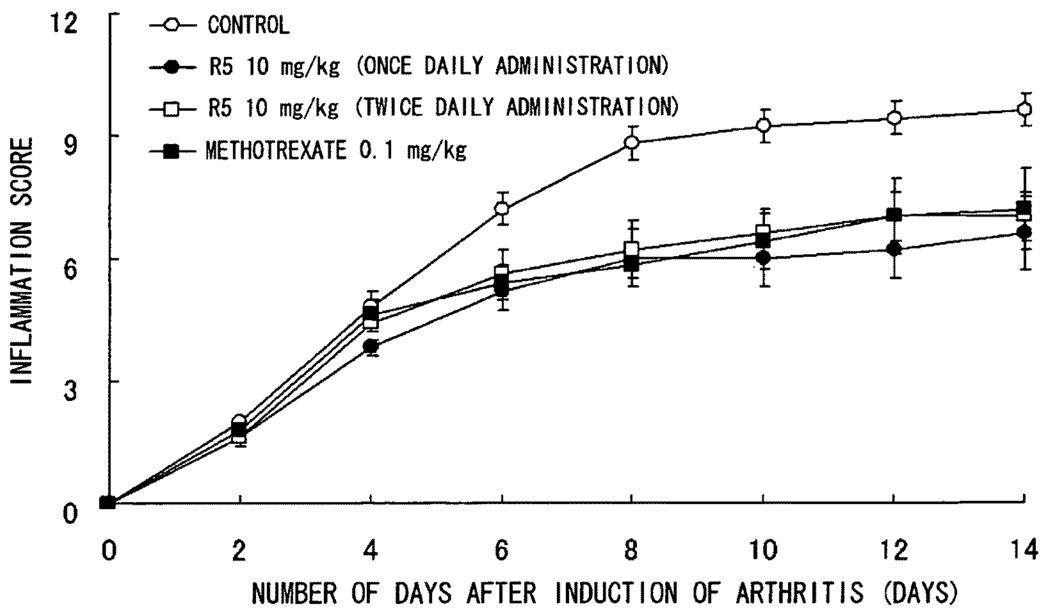
FIG. 3 shows that arthritis was inhibited in arthritis-induced mice by intraperitoneal administration (once daily administration or twice daily administration) of 10 mg/kg of peptide R5. As controls, the result for mice to which a peptide-free 0.5% methyl cellulose solution was administered once daily, and the result for mice to which 0.1 mg/kg of a methotrexate solution was administered once daily are shown.

The results are shown in FIG. 3. While no significant difference in the effectiveness of peptide R5 was observed between once daily administration and twice daily administration, an effect on arthritis inhibition was observed. In addition, the level of arthritis inhibition was higher than that of methotrexate. From this result, the peptide of the present invention was shown to have a better arthritis inhibitory action than the pharmaceutical products which are already clinically used, and to be useful for the treatment and prevention of arthritis and related diseases.

(2) Arthritis Inhibitory Action of a Peptide Capable of Binding to an Immunoglobulin on an Arthritis-Induced Mouse-2

Materials and Methods

The arthritis inhibitory action of the peptides indicated in Example 2 as R1, R2 and R5 was examined using monoclonal antibody cocktail-induced arthritis mice. An arthritis-inducing monoclonal antibody cocktail was intravenously administered at 2 mg/individual, and three days later, LPS was intraperitoneally administered at 50 μg/individual to the mice to induce arthritis. For each peptide, from the day the arthritis-inducing monoclonal antibody cocktail was administered (day 0), continuous administration was carried out at 10 mg/kg each, twice daily, for 14 days, and the arthritis inhibitory action was examined by clinical scoring. Note that the experiments were carried out by similar methods to Example 3 (1).

Preparation of Peptide Solution

Based on the animal body weight, the required amount of each peptide was calculated. A solution was prepared with a 0.5% methyl cellulose solution so as to reach a concentration of 1 mg/ml, and was stored refrigerated.

Body Weight Measurement and General State Observation

With the day the arthritis-inducing monoclonal antibody cocktail was administered as day 0, the animal's body weight was measured on day 0, 3, 6, 9, 12 and 14 during the test period. General state observation was carried out daily.

Preparation of Arthritis Model and Grouping

The body weight was measured on the day prior to starting administration and randomly assigned with a grouping software so that the average body weight value of each group was approximately the equal. To twenty 7 week-old mice, an arthritis-inducing monoclonal antibody cocktail were intravenously administered at 2 mg/individual on day 0, and LPS was intraperitoneally administered at 50 μg/individual on day 3.

Administration of the Peptide Solution

Each peptide solution was intraperitoneally administered twice daily, in the morning and in the afternoon, from day 0. As a control, 0.5% methyl cellulose solution was intraperitoneally administered twice daily from day 0. For administration, a syringe needle (26G, Terumo) and a syringe barrel (1.0 ml capacity, Terumo) were used. The dosage was 10 ml/kg.

Clinical Score Observation

With the day the arthritis-inducing monoclonal antibody cocktail was administered as day 0, on even days, clinical score for the extremities in all cases was observed until day 14 according to the followings. The score was 12 maximum in total for the extremities.

<Clinical Score>

0: normal articulation

1: slight inflammation and redness

2: serious erythema and swelling occupying the entirety of the limbs, interfering with the use of the limbs 3: deformation of the limbs or articulation accompanied by ankylosis, joint stiffness, loss of function Statistical Analysis Processing Method The test results were represented by mean value±standard error and the analysis was carried out using EXSAS (Version 7.1.6, Arm Systex Co., Ltd.). Wilcoxon test was carried out for the clinical score. Swelling of the legs was by direct visual observation.

Results

Figure 4:
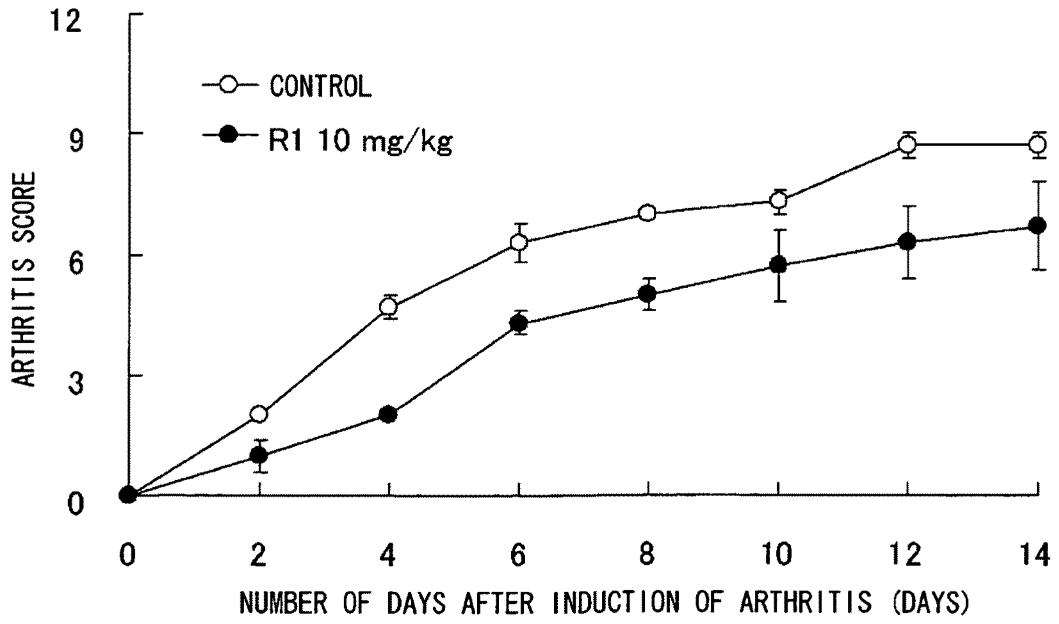
FIG. 4 shows that arthritis was inhibited in arthritis-induced mice by intraperitoneal administration of 10 mg/kg of peptide R1. As a control, the result for mice to which a peptide-free 0.5% methyl cellulose solution was administered similarly is shown.
Figure 5:
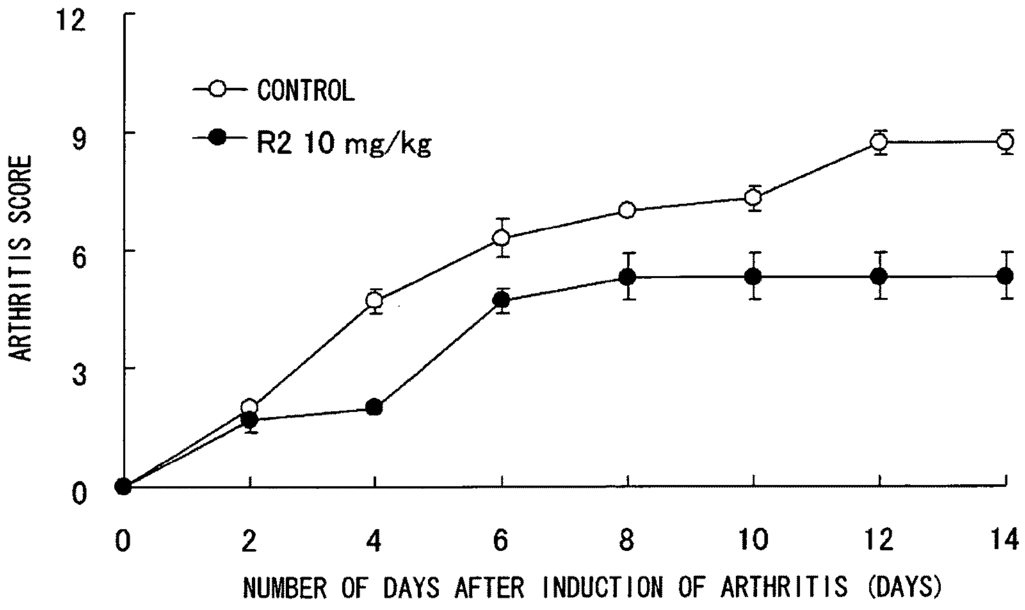
FIG. 5 shows that arthritis was inhibited in arthritis-induced mice by intraperitoneal administration of 10 mg/kg of peptide R2. As a control, the result for mice to which a peptide-free 0.5% methyl cellulose solution was administered similarly is shown.
Figure 6:
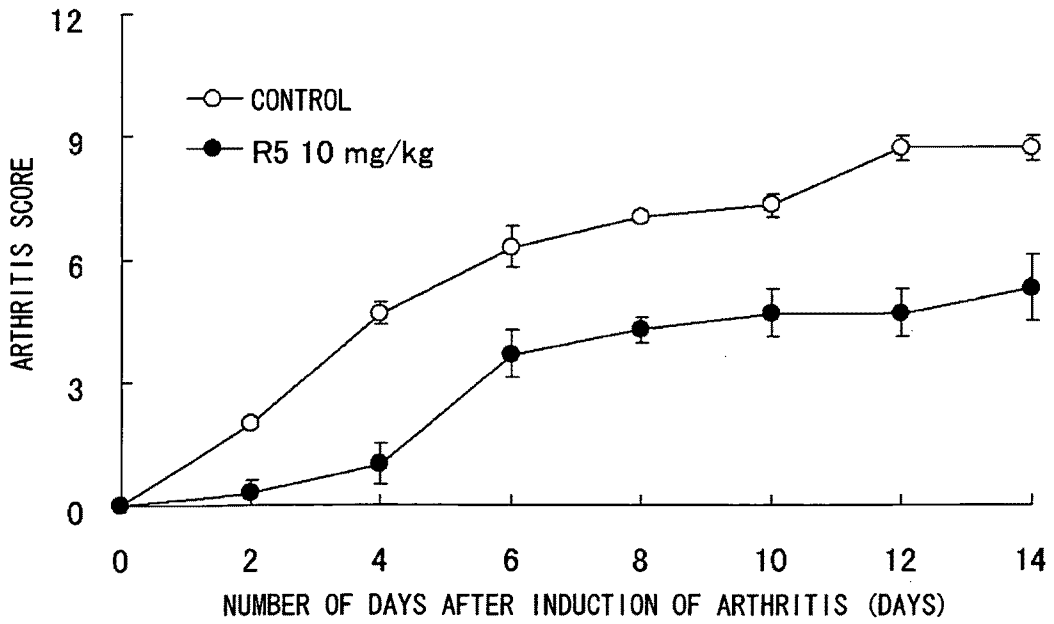
FIG. 6 shows that arthritis was inhibited in arthritis-induced mice by intraperitoneal administration of 10 mg/kg of peptide R5. As a control, the result for mice to which a peptide-free 0.5% methyl cellulose solution was administered similarly is shown.

The results are shown in FIG. 4, FIG. 5 and FIG. 6. Arthritis inhibitory action was observed in all the groups to which R1, R2 or R5 was administered at 10 mg/kg twice daily. Consequently, the peptide of the present invention was shown to have an arthritis inhibitory action, and to be useful for the treatment and prevention of arthritis and the related diseases. In addition, no anomaly of the general condition or action to body weight was observed in any of the peptides used.

Furthermore, the peptide of the present invention showed no toxic effect in the tests using mice. In addition, since the peptide of the present invention is derived from C1q which is naturally present inside a human body, and is short with 6 to 15 residues, it can be anticipated that adverse effects that are accompanied by a treatment or prophylaxis is decreased by using the peptide of the present invention.

EXAMPLE 4

Study of the Immune-Complex Disease Inhibitory Action of the Peptide Capable of Binding to an Immunoglobulin Materials and Methods The test for peptide R1, R2 and R5 using 64 male rats of the Slc:Wistar strain, which were 7 weeks old was carried out in twice, i.e. for each administration method (intraperitoneal administration and tail vein administration). Acclimation was carried out by giving normal solid chow CRF-1 for 9 days or longer. The day prior to administration, the dorsal hair of the animal was shaved, and on the administration day, a solution of OVA+Evans blue dye mix was administered into the tail vein. Each peptide solution was administered, 30 minutes after administration of a solution of OVA+Evans blue dye mix if administered intraperitoneally or 50 minutes after if administered into the tail vein, respectively. Regarding intracutaneous administration of anti-OVA solution, the solution was intradermally administered to the dorsal region of the animal at a dose of 0.1 ml/site, 30 minutes after administration of the test substance in case of intraperitoneal administration or 10 minutes after in case of intravenous administration, to induce locally an Arthus reaction. Four hours after the induction, the animals were euthanized, the blood was removed thoroughly, and then the dorsal skin was removed. The Arthus reaction site on the removed skin was punched out, and the Evans blue dye was extracted from this skin overnight. The amount of dye leaked was quantified by measuring the absorbance for Evans blue dye with a spectrophotometer and using a calibration curve (note that, regarding experimental methods used in Example 4, reference should be made to H. Okamoto, Y. Iwahisa and M. Terasawa: Suppression of the Arthus reaction by Y-24180, a potent and specific antagonist of platelet-activating factor. Agents Actions, 35: 149-158 (1992)).

Each peptide solution used in this experiment are shown below:

<Negative Control Substance>

Physiological Saline

<Peptide Solution>

The predetermined weighed amounts of each peptide (peptides R1, R2 and R5) were dissolved in physiological saline respectively to obtain a 20 mg/ml solution. A 2 mg/ml solution was prepared by diluting 10-fold a 20 mg/mL solutions with physiological saline. 5 mg/ml solutions were prepared by dissolving each peptide in predetermined weighed amounts in physiological saline to obtain preparation solutions.

Arthus Reaction

A solution of OVA+Evans blue dye mix was administered into the tail vein at 2 ml/kg. Each peptide solution was administered, 30 minutes after administration of the solution of OVA+Evans blue dye mix if administered intraperitoneally or 50 minutes after if administered into the tail vein, respectively. Regarding intracutaneous administration of anti-OVA solution, the solution was intradermally administered to the dorsal region of the animal at a dose of 0.1 ml/site, 30 minutes after administration of the test substance in case of intraperitoneal administration or 10 minutes after in case of intravenous administration, to induce locally an Arthus reaction. Intracutaneous administration was such that there were two PBS sites and two ant-OVA solution sites per animal. Four hours after the induction, the animals were euthanized by decapitation under ether anesthesia, the blood was removed thoroughly, and then the dorsal skin was removed. The Arthus reaction site on the removed skin was punched out with a punch and used for dye extraction.

Dye Extraction and Measurement

The skin strip that was punched out with a punch was slit at several locations, soaked in 2 ml of dye extraction solution, and shaken and agitated for 10 minutes. Thereafter, it was left standing overnight at room temperature. After it was left standing overnight, [the solution] was shaken again for 10 minutes, centrifuged (1500 rpm, 15 minutes), and the supernatant thereof was used as a sample for dye measurement. UV-1600 (Shimadzu Corporation) was used for the measurements, and the measurements were made at a wavelength OD 620 nm. The amount of dye leaked was calculated from the dye amount calibration curve.

Data Processing and Statistical Processing

The group mean values (mean)±standard deviation (SD) were calculated for the body weight measurement values and the amounts of dye leaked. Regarding the amount of dye leaked, the value for each animal was that obtained by subtracting the mean value of the two PBS administration sites from the mean value of the two anti-OVA solution administration sites. The following statistical analyses were carried out for the amounts of dye leaked: in the first test (intraperitoneal administration of each peptide solution), Bartlett's test for homogeneity of variances were carried out for each of the first group against the second and third groups, the first group against the fourth and fifth groups, and the first group against the sixth and seventh groups, and the difference in the mean values was tested between the first group and each of the other groups by Dunnett's multiple comparison test if there was no difference in the variances or by Steel's multiple comparison test if there was a difference in the variances; in the second test (tail vein administration of each peptide solution), Bartlett's tests for equal variances were carried out among the ninth group against the tenth, eleventh and twelfth groups, and the difference in the mean values was tested between the ninth group and each of the other groups by Dunnett's multiple comparison test if there was no difference in the variances or by Steel's multiple comparison test if there was a difference in the variances. The level of significance was 5% in the Bartlett's test for homogeneity of variances, and 5% on both sides in the other assays.

Results

Figure 7:
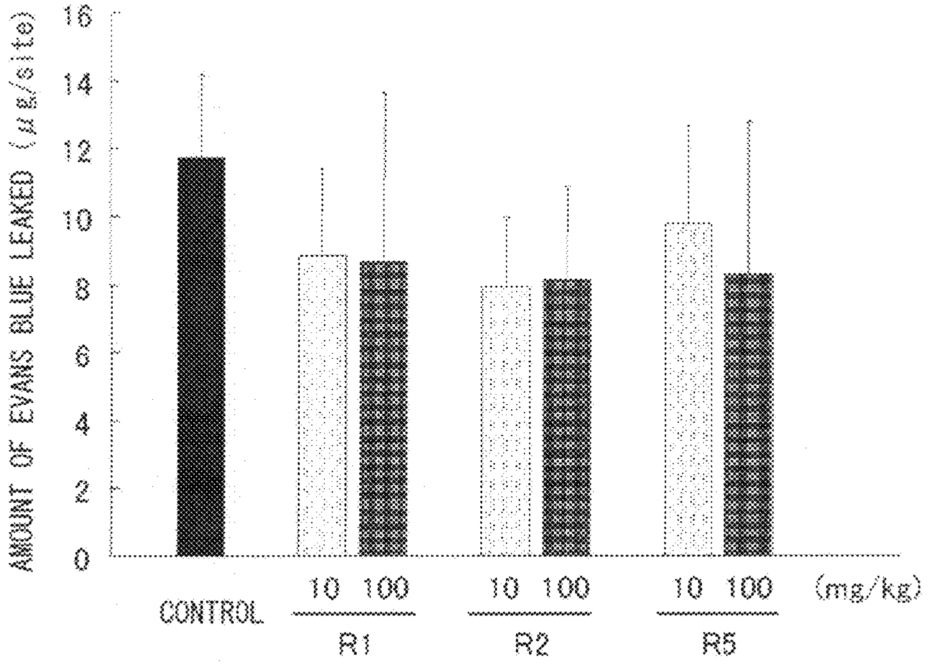
FIG. 7 shows that immune-complex diseases such as SLE, glomerulonephritis, vasculitis or arthritis were inhibited in a Type III allergic (Arthus) reaction-induced rat by intraperitoneal administration of 10 mg/kg or 100 mg/kg of peptide R1, R2 or R5. As a control, the result for a rat to which a peptide-free physiological saline was administered similarly is shown.
Figure 8:
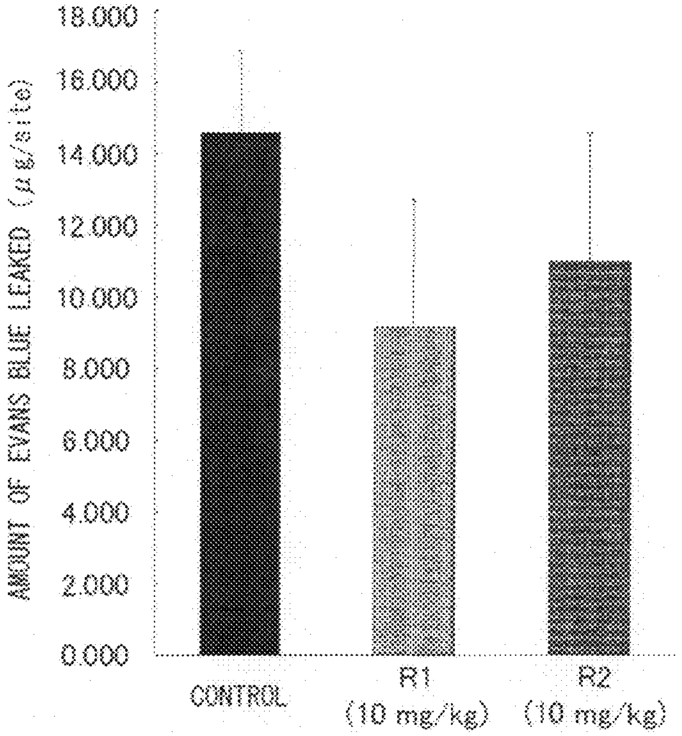
FIG. 8 shows that immune-complex diseases such as SLE, glomerulonephritis, vasculitis or arthritis were inhibited in a Type III allergic (Arthus) reaction-induced rat by administration of 10 mg/kg of peptide R1 or R2 in the tail vein. As a control, the result for a rat to which a peptide-free physiological saline was administered similarly is shown.

For each peptide solution, the results of intraperitoneal administration are shown in FIG. 7, and the results of tail vein administration are shown in FIG. 8 respectively. In the Type III allergic (Arthus) reaction model system used in the present example, a decrease in Evans blue leakage of approximate 30% compared to the controls was observed, which was deemed effective for inhibiting immune-complex diseases such as SLE, glomerulonephritis, arthritis or vasculitis and others. In intraperitoneal administration of peptide solutions, a clear and sufficient inhibitory action on immune-complex disease was observed for all the peptides R1, R2 and R5. In addition, in tail vein administration, a clear and sufficient inhibitory action on immune-complex disease was observed for peptide R1 and R2. Consequently, the peptide of the present invention was shown to have a clear and sufficient inhibitory action on immune-complex disease and to be useful for the treatment and prevention of immune-complex diseases such as SLE, glomerulonephritis, arthritis or vasculitis.

EXAMPLE 5

Examination of an Antibody Detection Agent that Uses a Peptide Capable of Binding to an Immunoglobulin Materials and Methods Whether a primary antibody in a western-blot could be detected using a biotinylated peptide instead of secondary antibody was examined. Peptide R5 that was biotinylated was prepared by outsourcing to GL Biochem (Shanghai).

BSA was electrophoresed in 12% SDS-PAGE and transcribed onto a PVDF membrane. The PVDF membrane after transcription was blocked in 5% skim milk. The PVDF membrane was soaked in a solution of 2000-fold diluted anti-BSA IgG (rabbit) and reacted at room temperature for one hour. Washing were carried out three times in TBST. Biotinylated peptide R5 was dissolved in DMSO so as to reach a concentration of 10 mg/ml, 10 ul of this solution was added to 10 ml of TBST (1000-fold dilution), and reacted at room temperature for one hour. Washing were carried out three times in TBST. Coloring was carried out using ABC kit manufactured by VECTOR laboratories. Nickel sulfate and diaminobenzidine were used in the coloring solution and hydrogen peroxide solution was used for the substrate.

Results

Figure 9:
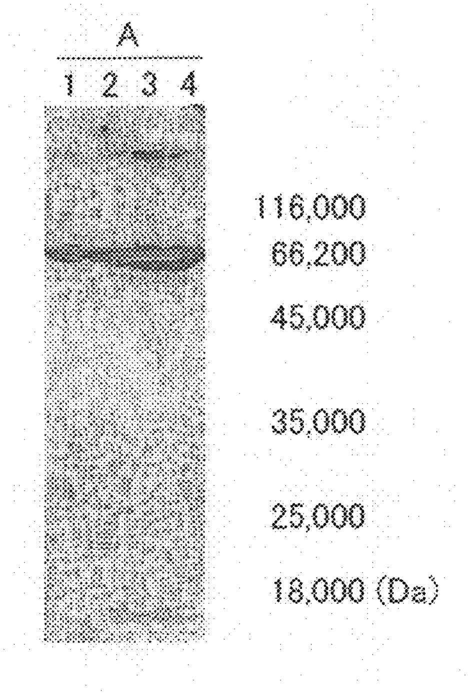
FIG. 9 shows that the antibody was detected with the peptide of the present invention. For each lane, the following amount of BSA was used: lane 1, 0.1 μg BSA; lane 2, 0.5 μg BSA; lane 3, 1.0 μg BSA; and lane 4, 2.0 μg BSA.

The results are shown in FIG. 9. An antibody on the PVDF membrane could be detected using a biotinylated peptide of the present invention instead of a secondary antibody. Consequently, the peptide of the present invention that was biotinylated was shown to be useful in the detection of an antibody.

EXAMPLE 6

Examination of an Antibody Purification Column that Uses a Peptide Capable of Binding to an Immunoglobulin Materials and Methods An antibody purification column that uses a peptide capable of binding to an immunoglobulin was examined. Note that Protein A was used as a control.

Preparation of a Peptide Column

A PD-10 Empty column was filled with 1 ml of NHS-activated Sepharose 4B Fast Flow, washed with 10 ml of 1 mM HCl and equilibrated with 10 ml of PBS. 5 mg of peptide R4 dissolved in 1 ml of PBS was added to the column, which was rotated at room temperature for four hours. The column was washed with 5 ml of PBS, then, 1 ml of 1 M glycine was added, and [the column was] rotated at room temperature for two hours to block unreacted NHS. The 1 M glycine was removed and [the column was] equilibrated by washing with 10 ml of PBS.

Purification of Antibody

To an affinity purification column, 1 mg of anti-BSA IgG (rabbit) (anti-bovine serum albumin IgG (rabbit)) was added, and [the column was] rotated at room temperature for two hours. Washing was carried out with 15 ml of PBS. Anti-BSA IgG was eluted by adding 5 ml of 0.1 M glycine-HCl (pH 3.2) and collected in five microtubes of 1 ml containing 100 ul of 1 M Tris. The amount of protein in the elution fractions was quantified with the DC Protein Assay Kit (Bio-Rad). In addition, a similar adsorption-elution test was carried out for human IgG.

Results

Figure 10:
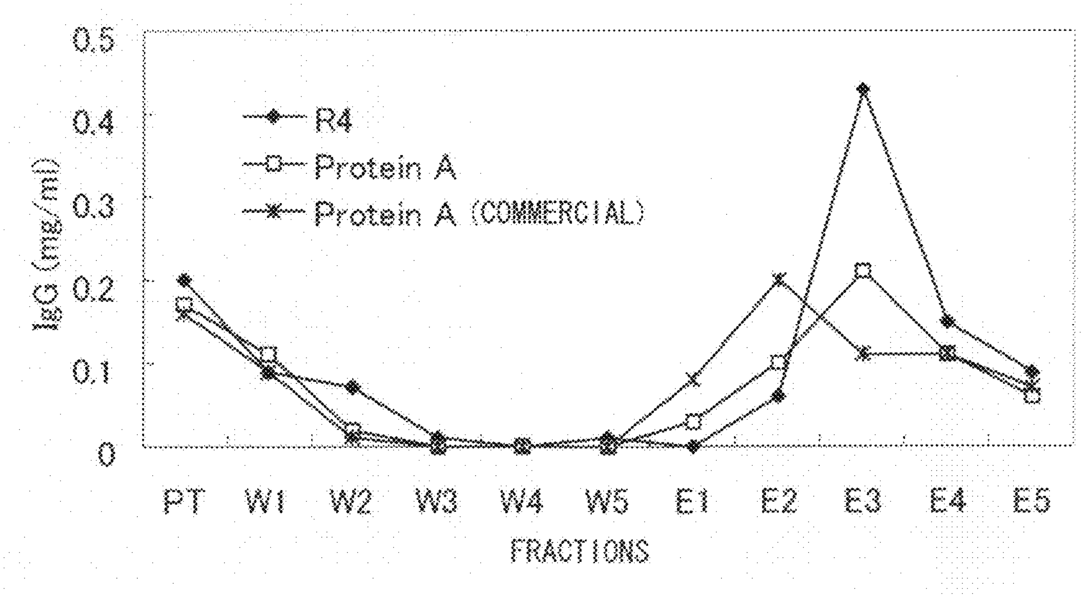
FIG. 10 shows that a rabbit antibody was purified by an affinity purification column that uses the peptide of the present invention. As a control, the result of purification using Protein A is shown. The values indicate the amount of IgG protein (mg/ml) in each fraction. In the figure, PT represents flow-through fractions, W1 to 5 represent wash fractions, and E1 to 5 represent elution fractions.
Figure 11:
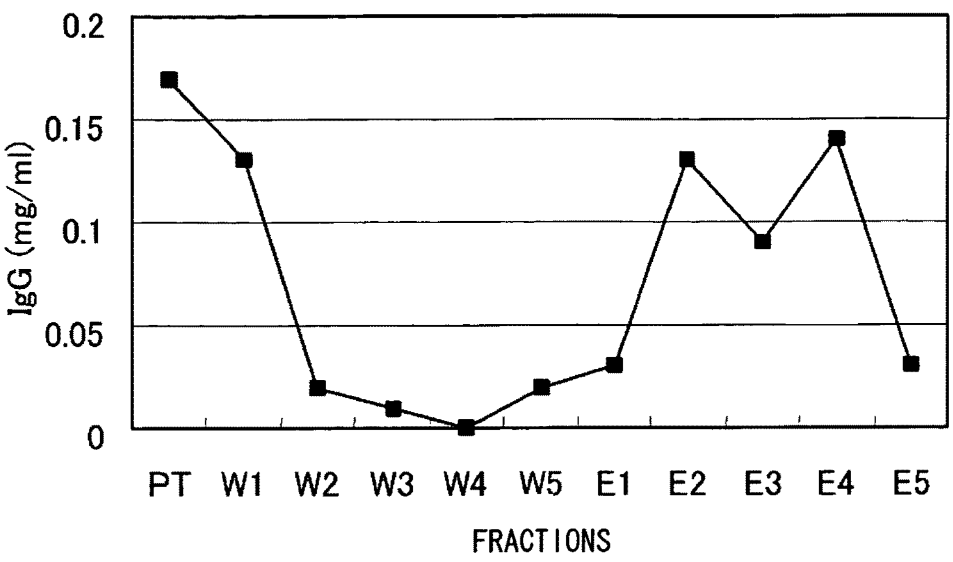
FIG. 11 shows that a human antibody was purified by an affinity purification column that uses the peptide of the present invention. The values indicate the amount of IgG protein (mg/ml) in each fraction. In the figure, PT represents flow-through fractions, W1 to 5 represent wash fractions, and E1 to 5 represent elution fractions.

The results are shown in FIG. 10. In the column that used the peptide of the present invention, 70 to 80% of the rabbit antibodies used in the purification were recovered. This recovery rate was better than that of the control Protein A. In addition, the affinity purification column that used the peptide of the present invention was shown to be usable also for the purification of human IgG (FIG. 11). Consequently, the means in which the peptide of the present invention was immobilized was shown to be extremely useful in antibody purification.

INDUSTRIAL APPLICABILITY

According to the present invention, a peptide capable of binding to an immunoglobulin and such a fusion protein of the peptide, nucleic acids encoding the peptide and the fusion protein, and others are obtained, thus, the invention can be used in the fields of detection, isolation and purification of immunoglobulins, and of pharmaceutical composition for the treatment or prevention of a disease induced by the binding between C1q and an immunoglobulin such as rheumatoid arthritis or immune-complex diseases such as SLE, glomerulonephritis, vasculitis or arthritis.

SEQUENCE LISTING FREE TEXT

SEQ ID NO: 1: Immunoglobulin binding peptide
SEQ ID NO: 2: Immunoglobulin binding peptide
SEQ ID NO: 3: Immunoglobulin binding peptide
SEQ ID NO: 4: Immunoglobulin binding peptide
SEQ ID NO: 5: Immunoglobulin binding peptide
SEQ ID NO: 6: Immunoglobulin binding peptide
SEQ ID NO: 7: Immunoglobulin binding peptide
SEQ ID NO: 23: Immunoglobulin binding peptide
SEQ ID NO: 24: Immunoglobulin binding peptide
SEQ ID NO: 25: Immunoglobulin binding peptide
SEQ ID NO: 26: Immunoglobulin binding peptide
SEQ ID NO: 27: Immunoglobulin binding peptide

The invention claimed is:

1. An isolated peptide capable of binding to an immunoglobulin, wherein the isolated peptide consists of SEQ ID NO:1.

2. An isolated nucleic acid encoding the peptide consisting of SEQ ID NO:1.

3. The isolated nucleic acid of claim 2, wherein the nucleic acid consists of SEQ ID NO:8.

4. A vector comprising the nucleic acid according to claim 2.

5. An isolated host cell comprising the nucleic acid of claim 2, or a vector comprising the nucleic acid of claim 2.

6. An isolated peptide capable of binding to an immunoglobulin, wherein the peptide consists of SEQ ID NO:1, and wherein the peptide is obtained by a method comprising the steps of:

(a) transforming a cell with a vector encoding the peptide consisting of SEQ ID NO:1; and (b) culturing the cell to produce the peptide consisting of SEQ ID NO:1.

7. A composition for binding an immunoglobulin, comprising the isolated peptide consisting of SEQ ID NO:1.

8. An article of manufacture, comprising a carrier having immobilized thereon the isolated peptide consisting of SEQ ID NO:1.

9. A kit, comprising (1) the isolated peptide consisting of SEQ ID NO:1 and (2) a label.

10. A pharmaceutical composition comprising the isolated peptide consisting of SEQ ID NO:1.

11. An isolated peptide consisting of SEQ ID NO:1, wherein the peptide is labeled.

* * * * *